United States Patent [19]
Lorin et al.

[11] Patent Number: 4,482,581
[45] Date of Patent: Nov. 13, 1984

[54] PROCESS FOR THE PRODUCTION OF A CAPACITIVE HYGROMETER

[75] Inventors: André Lorin, Orsay; André Rosilio, Antony; Jean Tanguy, Paris, all of France

[73] Assignee: Commissariat a l'Energie Atomique, Paris, France

[21] Appl. No.: 340,732

[22] Filed: Jan. 19, 1982

[30] Foreign Application Priority Data

Jan. 19, 1981 [FR] France ................. 81 00890

[51] Int. Cl.³ .................. B05D 5/12; H01L 7/00
[52] U.S. Cl. .................. 427/79; 427/93; 427/383.5; 427/383.3; 427/383.1; 338/35; 361/286
[58] Field of Search .......... 427/79, 93, 383.5, 383.3, 427/383.1; 338/35; 361/286

[56] References Cited
U.S. PATENT DOCUMENTS 4,203,087 5/1980 Kovac .................. 338/35

Primary Examiner—John E. Kittle
Assistant Examiner—James J. Seidleck
Attorney, Agent, or Firm—Pearne, Gordon, Sessions, McCoy, Granger & Tilberry

[57] ABSTRACT

The present invention relates to a process for producing a capacitive hygrometer, as well as to a hygrometer obtained by this process.

Onto a conductive layer forming the first electrode is deposited a layer of a material with a dielectric constant varying as a function of the quantity of water absorbed. Onto the said dielectric material layer is then deposited a layer with a thickness exceeding 200 Å of a slightly oxidizable metal, which forms the second electrode. The latter is made permeable to water by heat treatment at a temperature close to the softening temperature of the dielectric.

Application to the measurement of the relative humidity of air.

24 Claims, 4 Drawing Figures

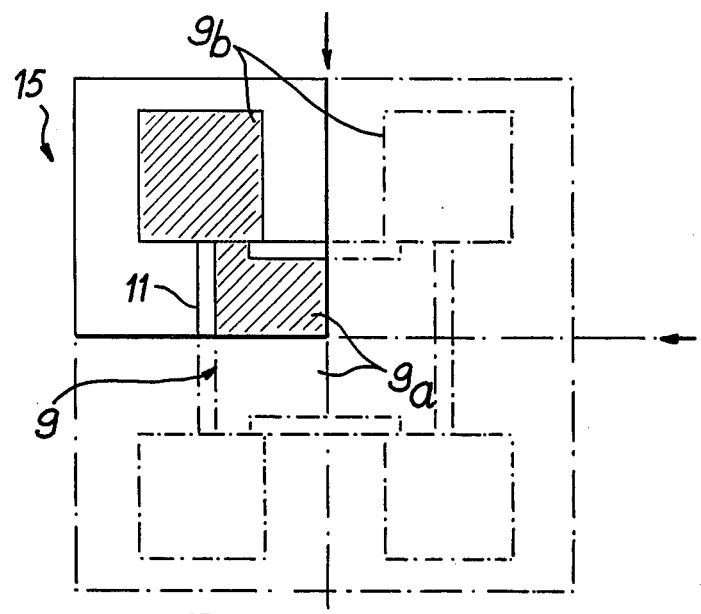
FIG.3
FIG.4
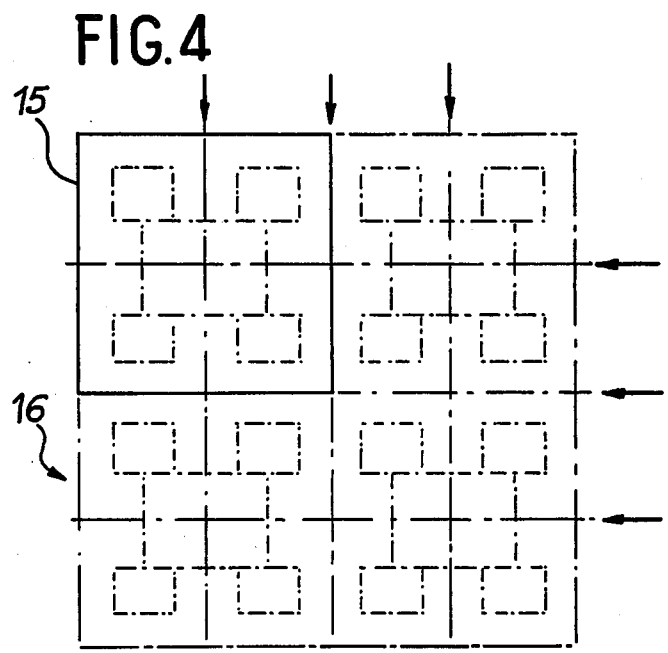

PROCESS FOR THE PRODUCTION OF A CAPACITIVE HYGROMETER

BACKGROUND OF THE INVENTION

The invention relates to a process for the production of a thin dielectric capacitive hygrometer, as well as to a hygrometer obtained by this process.

For measuring the humidity of the air, it is known to use the variations of the dielectric constant of a thin layer material constituting the dielectric of a capacitor as a function of the quantity of water absorbed.

A certain number of devices functioning on the basis of this principle already exist and have been described in the literature. Reference is made in this connection to U.S. Pat. Nos. 3,168,829 (Nelson) and 3,350,941 (Misevich et al), British Pat. No. 1,297,014, the Article by K. W. Misevich in IEEE Trans. and Ind. Electronics and Control Instrumentation, Vol. IECI 16, No. 1, July 1969, Finnish Pat. No. 2,831,72 of the Vaisala Company, French Patent No. 73 36153 of the same company and corresponding to the aforementioned Finnish Patent, French Pat. No. 76 01904 of the Commissariat à l'Energie Atomique (Barraud, Messier, Rosilio), the Article by E. Salasma and P. Kestamo of the Vaisala Company (3rd Symposium on Meteorological Observations, February 1973, Washington), the Article by P. E. THOMA, J. O. COLLA and R. STEWART in IEEE Trans. on Comp Hybrids and Manufact. Technology, Vol. CHAT, No. 3, Sept. 1979 and finally the 1974 U.S. Pat. No. 3,802,268 of P. E. THOMA.

These different hygrometers or humidity measuring devices can be placed in two categories. The first category (Misevich, Nelson, Thoma) is characterized by the fact that the dielectric material is formed by a polymer sheet serving both as the sensitive element and as the mechanical support for the hygrometer. This leads to a certain number of disadvantages for this type of hygrometer, i.e. limited mechanical strength, deformation of the polymer leading to a significant hysteresis effect and a certain temperature coefficient.

The hygrometers of the second type are formed from a polymer layer (Vaisala) or other water-sensitive molecules (Barraud et al) deposited on a metallized solid substrate forming the first electrode of a capacitor. Thus, the mechanical support of the hygrometer, generally made from glass or some other moisture-inert material, is separate from the water-sensitive layer.

This arrangement makes it possible to overcome the defects of the first type (mechanical strength, hysteresis, slow response, temperature coefficient), but the second electrode of the capacitor must be very thin to enable it to be permeable to water. This makes it necessary to take certain precautions during manufacture and leads to a certain lack of strength on the part of the hygrometer. In addition, the thinness of the electrode makes it sensitive to pollution, which reduces the service life of the device. Finally, it is a difficult operation to deposit the polymer film, because the latter must be free from defects or holes in order to prevent any danger of short-circuiting between the electrodes. However, to obviate this danger, it is necessary to place a thin insulating layer, which is insensitive to water between the first electrode and the polymer layer. This prevents short-circuits in the case of any perforation of the dielectric without modifying the sensitivity of the hygrometer, because the insulating layer has a significant capacitance.

BRIEF SUMMARY OF THE INVENTION

The present invention relates to a process for the production of a capacitive hygrometer which eliminates the disadvantages referred to hereinbefore, whilst making it possible to use as the water-permeable electrode a metal layer which is sufficiently thick to have a good mechanical strength.

Thus, the present invention specifically relates to a process for the production of a thin dielectric capacitive hygrometer of the type in which onto a layer of a conductive material forming the first electrode is deposited a layer of insulating material, whose dielectric constant varies with the quantity of water absorbed, then on said dielectric material layer is deposited a second metallic layer forming the second electrode, which is made permeable to water, wherein for producing said second electrode, onto the dielectric layer is deposited at least one layer having a thickness greater than 200 Å of a slightly oxidizable metal, which then undergoes a heat treatment at a temperature close to the softening temperature of the material forming the dielectric layer in order to make the the second metallic layer permeable to water.

The dielectric softening temperature is generally close to melting point. This treatment leads to a modification of the structure of the material forming the dielectric, which leads to a permanent deformation of the second electrode, which assumes a granular structure with grains of approximately 1 micron. This leads to a good porosity of the metallic layer, which becomes permeable to water vapour, whilst retaining a good mechanical strength, particularly with respect to sudden temperature changes.

BRIEF DESCRIPTION OF THE DRAWINGS

The invention is described in greater detail hereinafter relative to non-limitative embodiments and with reference to the attached drawings, wherein show:

FIG. 3 a diagrammatic plan view showing how it is possible to produce four hygrometers from a single small plate.

FIG. 4 a diagrammatic plan view showing how it is possible to produce 16 hygrometers from a single small plate.

DETAILED DESCRIPTION OF THE PREFERRED EMBODIMENTS

Figure 1:
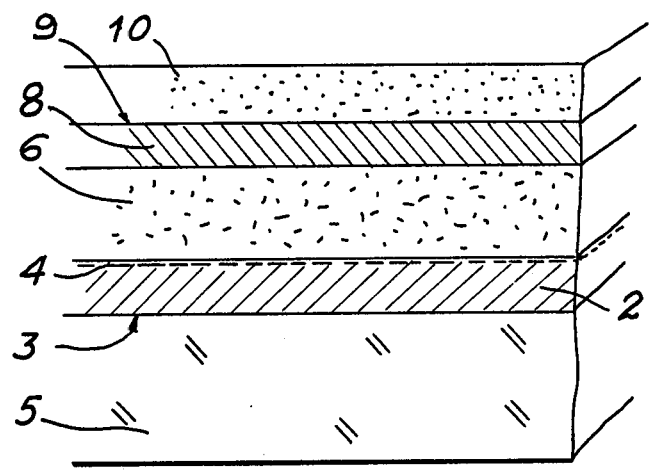
FIG. 1 a diagrammatic perspective view of a capacitive hygrometer as obtained by the process of the invention.

FIG. 1 shows a metallic substrate 2 constituting the first electrode 3 of a capacitive hygrometer. In the embodiment shown here, electrode 3 is made from aluminium and rests on a rigid support 5, e.g. a glass plate. However, it is also possible to use a relatively thick conductive layer, e.g. a layer of silicon, which in itself forms a rigid support.

In most cases, one of the faces 4 of the first electrode is oxidized over a depth of approximately 50 to 200 Å and this face is in contact with a layer 6 of insulating material forming the dielectric of the capacitor and whose dielectric constant varies as a function of the quantity of water absorbed.

The advantage obtained with a dielectric formed from two superimposed parts, one being insensitive to water and having a very limited thickness (of 50 to 200 Å) e.g. of aluminium oxide or silicon oxide and the other having a greater thickness (500 to 2000 Å) and sensitive to moisture is that a very effective protection is obtained against possible short-circuiting of the water-sensitive layer. As the capacitance of the oxide layer is very high, its arrangement in series with that of the active dielectric virtually leads to no reduction in the sensitivity of the hygrometer. It is therefore possible to form hygrometers with a short response time having a high specific capacitance in spite of the fact that they are protected against short-circuits by the oxide layer. The specific capacitance of such hygrometers is approximately 10 to 20 nF/cm$^2$, i.e. higher than that of most presently used capacitive hygrometers.

The insulating material with a dielectric constant which varies as a function of the quantity of water absorbed can be constituted by a polymer which is naturally sensitive to water, such as cellulose esters, cellulose acetobutyrate or polyvinylacetate. It is also possible to use polymers which can assume a cross-linked structure under the action of heat or ultraviolet radiation, e.g. cellulose acetocrotonate or cellulose acetobutyrocrotonate. In this way, hygrometers are obtained, which have a particularly good resistance to heat and mechanical agents (acids, solvents, pollutants, etc).

It is also possible to use a superimposing of monomolecular layers of an organic substance deposited in accordance with the so-called Langmuir and Blodgett method, said layers then being made sensitive to water by an appropriate treatment.

FIG. 1 also shows a metallic layer 8 constituting the second electrode 9. The latter is preferably formed by a slightly oxidizable metal such as gold deposited in the form of a relatively thick layer (exceeding 200 Å) and made permeable to water by a subsequent treatment.

The hygrometer may optionally comprise one or more monomolecular layers of an organic substance 10, which protects the permeable electrode from corrosion, but the presence of these monomolecular layers is not indispensible.

Figure 2:
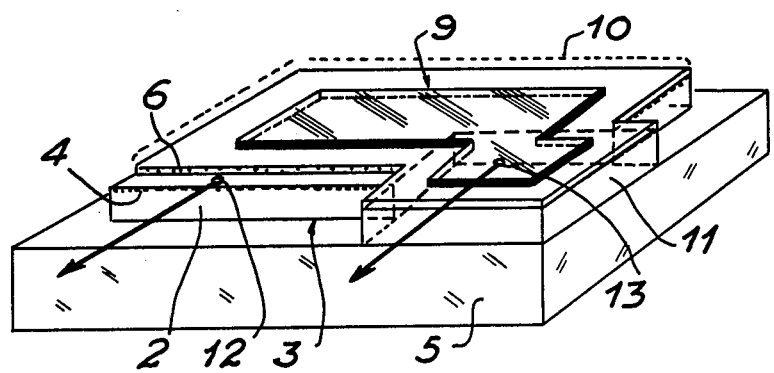
FIG. 2 a diagrammatic perspective view illustrating one embodiment of the process according to the invention.

FIG. 2 illustrates an embodiment of the process according to the invention. An aluminium layer 2 is deposited, e.g. by vacuum evaporation on a glass support 5. An insulating bloc, next to layer 2, e.g. of silicon oxide, is then deposited at 11. In the case of FIG. 2, one of the angles of electrode 2 has been notched to enable insulating block 11 to be placed in the notch and in contact with electrode 2. The thickness of block 11 is substantially the same as that of electrode 2 in order that the dielectric material 6 can be deposited on the planar surface formed by electrode 2 and block 11. The function of the latter will be described in greater detail hereinafter. During the manufacturing stage, the aluminum layer undergoes an anodic oxidation treatment in order to form the thin alumina layer 4.

The following stage consists of depositing the layer 6 of water-sensitive insulating material. In the case when a polymer is used (e.g. cellulose acetobutyrate) the oxidized metallic substrate can be immersed in a solution of the polymer and a solvent, followed by drying. In this way, a layer of thickness 1000 to 2000 Å is obtained.

In the case when the dielectric is formed by organic monomolecular layers, the latter are deposited by the Langmuir and Blodgett method and the layer then has a thickness of approximately 500 Å. An organic substance such as calcium stearate is very suitable for this purpose. However, the dielectric obtained in this way is not naturally permeable to water and it must be made permeable by a special treatment consisting of irradiation with gamma rays or electrons. In accordance with a preferred embodiment, gamma rays from a cobalt 60 source are used. The absorbed dose is approximately 40 Mrads and in all cases exceeds 20 Mrads, said dose being absorbed during a period exceeding 1 hour.

The second stage consists of producing the second electrode 9, which can be in the form of a gold coating whose thickness exceeds 200 Å and which is deposited by any per se known method and particularly vacuum metallization. On the basis of its thickness, said gold coating is not permeable to water. According to the invention, it is made permeable by subjecting the hygrometer to a heat treatment at a temperature close to the softening point of the dielectric. Most of the materials used for forming the dielectric layer have softening temperatures between 150° and 250° C., i.e. close to their melting point. It is merely necessary to expose the hygrometer to this temperature under normal atmospheric conditions for a few minutes, with the capacitor dead in order to obtain a change in the structure of the dielectric leading to a permanent deformation of the gold coating. The latter assumes a granular structure with grains between 0.1 and 5 microns and generally close to 1 micron. These grains and porosities are visible under the microscope (optical and electronic) and show that the hygrometer has indeed been produced by the process according to the invention. If desired, the protective layer for the second electrode is then produced and is in the form of one or more monomolecular layers of an organic substance deposited by the Langmuir and Blodgett process.

The hygrometer is finished by producing electrical contacts with the two electrodes 3 and 9. In FIG. 2, it is possible to see that the dielectric layer 6 does not entirely cover electrode 4, which makes it possible to directly weld the first contact 12 to the exposed part of electrode 4, through the superficial oxide layer. The permeable electrode 9 extends over layer 6 both above the first electrode 4 and above insulating bloc 11. The second electrical contact 13 is welded to that part of electrode 9 positioned above block 11.

It is also possible to use other methods for producing electrical contacts. In the case when the first electrode is a metallic layer deposited on a glass substrate and when the dielectric is a polymer with a low melting point (melting point below 250° C.), said contacts can be welded through the polymer. Thus, the dielectric layer 6 can entirely cover the first electrode 3 because the polymer melts when the first contact 12 is welded and the second contact 13 can be welded so as to straddle the second electrode 9 and insulating block 11. When using a polymer with a high melting point (exceeding 300° C.), the second contact 13 is welded to electrode 9 in the manner which is shown in FIG. 2, and it is necessary to eliminate the polymer, e.g. by etching before welding the first contact 12.

If a silicon block is used as the first electrode, the first contact is formed directly on the conductive substrate without welding. In this case, if the polymer has a high melting point, it is possible to eliminate the insulating block 11 and weld the second contact to the upper electrode 9. If the polymer has a low melting point, the second contact is welded so as to straddle the permeable electrode and an insulating block.

The use of a silicon substrate leads to the obviating of a welding process for one of the contacts and consequently simplifies the construction of the apparatus. It also permits greater miniaturization of the hygrometer.

FIG. 3 shows an arrangement making it possible to produce several hygrometers from a single member 15, which is cut in the manner indicated by the arrows. The first electrode is deposited as if member 15 constituted a single hygrometer. However, insulating block 11 is placed in the centre of member 15 so as to extend over each of the hygrometers which are obtained after cutting (four in the present embodiment). The second electrode 9 has a portion 9a extending over most of block 11 and portions 9b corresponding to each of the hygrometers.

FIG. 4 illustrates a method making it possible to produce a large number of hygrometers from a support 16 in which several members, like member 15 described with reference to FIG. 3 are produced.

The process according to the invention offers numerous advantages. Firstly, the fact that the second electrode is formed by a thick metallic layer made permeable to water by an appropriate treatment eliminates all the disadvantages of thin electrodes by facilitating the production process and by making the electrode less sensitive to pollution, which increases the life of the hygrometer. In addition, the presence on the first electrode of an oxide layer constituting a second dielectric in series with the water-sensitive insulating material prevents short-circuits between the electrodes, makes it possible to use a very thin water-sensitive material and gives the assembly a greater specific capacitance permitting a good connection with the means for measuring the dielectric constant. Finally, the presence of a thin dielectric leads to the hygrometer having a very high response speed. A standard test (at 63% of the maximum amplitude for 100% moisture content) has given a response time below 0.5 sec., whilst this time is several seconds in the case of existing standard hygrometers.

Obviously, the invention is not limited to the embodiments described and numerous variants are possible thereof without passing beyond the scope of the invention. Thus, the permeable electrode can be produced from gold or some other slightly oxidizable metal, such as chromium or nickel. It is also possible to use several layers of different metals chosen from among the aforementioned metals, for instance a layer of nickel covered with gold or a three layer deposition of chromium, nickel and gold.

The applications are not limited to measuring the relative humidity of air. Thus, the devices according to the invention can be used for measuring any magnitude, whose variation leads to a variation of the dielectric constant of the insulating material.

What is claimed is:

1. A process for the production of a thin dielectric capacitive hygrometer of the type in which onto a layer of a conductive material forming the first electrode is deposited a layer of insulating material, whose dielectric constant varies with the quantity of water absorbed, then on said dielectric material layer is deposited a second metallic layer forming the second electrode, which is made permeable to water, wherein for producing said second electrode, onto the dielectric layer is deposited at least one layer having a thickness greater than 200 Å of a slightly oxidizable metal, which then undergoes a heat treatment at a temperature close to the softening temperature of the material forming the dielectric layer in order to make the layer permeable to water.

2. A process according to claim 1, wherein a metal chosen from the group consisting of gold, nickel and chromium is used for producing the layer forming the second electrode.

3. A process according to claim 1, wherein several layers of different metals chosen from the group comprising gold, nickel and chromium are deposited for producing the second electrode.

4. A process according to claim 1, wherein the metallic layer forming the first electrode undergoes an oxidation treatment for forming an oxide layer on the face of said electrode, which must be in contact with the dielectric.

5. A process according to claim 1, wherein the first electrode is deposited on a rigid insulating support.

6. A process according to claim 5, wherein it comprises the further steps of depositing a metallic layer forming the first electrode on the rigid support and next to said layer is deposited an insulating block with a thickness which is substantially the same as that of the layer, the dielectric material is deposited both on the first metallic layer and on the insulating block, the second metallic layer is deposited on the dielectric layer and a first and a second electrical contact is provided with the first and second electrodes respectively.

7. A process according to one of the claims 5 or 6, wherein a polymer with a melting point equal to or below 250° C. is used for forming the dielectric layer.

8. A process according to claim 7, wherein the shape given to the second electrode is such that it extends partly over the insulating block and only partly covers the first electrode, the second electrical contact being welded so as to straddle the second electrode and insulating block through the polymer, whilst the first electrical contact is welded to the first electrode through the polymer.

9. A process according to claims 5 or 6, wherein a polymer with a melting point equal to or above 300° C. is used for forming the dielectric layer.

10. A process according to claim 9, wherein the second electrode is shaped in such a way that it extends partly over the insulating block and only partly covers the first electrode, the second electrical contact being welded to the metal constituting the second electrode and the first electrical contact being welded to the first electrode after etching the polymer.

11. A process according to claim 1, wherein the first conducting layer forming the first electrode has a thickness which is adequate to enable it to form a rigid support.

12. A process according to claim 11, wherein the first electrode is formed by a silicon layer.

13. A process according to claims 11 or 12, wherein a polymer with a melting point equal to or below 250° C. is used for forming the dielectric layer.

14. A process according to claim 13, wherein it comprises arranging an insulating block in contact with the support forming the first electrode, depositing the dielectric layer both on the support and on the insulating block, depositing the metallic layer forming the second electrode on the dielectric layer in such a way that it only partly covers the insulating block and welding the second electrical contact so as to straddle the second electrode and the insulating block through the dielectric material, the first contact being produced directly on the support.

15. A process according to claims 11 or 12, wherein a polymer with a melting point equal to or above 300° C. is used for forming the dielectric layer.

16. A process according to claim 15, wherein the second electrical contact is welded to the second electrode, whilst the first contact is produced directly on the first electrode.

17. A process according to claim 1, wherein the dielectric layer is formed from a polymer which can assume a cross-linked structure under the action of heat or ultraviolet radiation.

18. A process according to claim 17, wherein the dielectric material is chosen from the group comprising cellulose acetocrotonate and cellulose acetobutyrocrotonate.

19. A process according to claim 1, wherein four hygrometers are produced from a single member, which is cut after depositing the metallic layer forming the second electrode in such a way that it extends over the four hygrometers cut from the member.

20. A process according to claim 19, wherein a large number of hygrometers is produced from a single support, which is cut in order to obtain members according to claim 19.

21. A hygrometer obtained by the process according to any one of the claims 1, 2, 3, 4, 5, 6, 11, 12, 17, 18, 19 or 20, wherein the second electrode has a granular structure, whose grains are between 0.1 and 5 microns.

22. A process for the production of a capacitive hygrometer, of the type in which onto a layer of a conductive material forming the first electrode is deposited a layer of insulating material comprising a polymer whose dielectric constant varies with the quantity of water absorbed, then on said dielectric material layer is deposited a second conductive layer forming the second electrode which is made peremable to water, wherein it comprises the steps of depositing a metallic layer forming the first electrode on a rigid support, depositing next to said layer an insulating block, depositing the dielectric material on substantially the entire extent of the first metallic layer and on the insulating block, depositing the second conductive layer on the dielectric layer so that at least one part of the second conductive layer extends over the insulating block forming an oxide layer on the face of one of said electrodes adjacent said dielectric layer, and producing first and second electrical contacts with the first and second electrodes respectively, said second contact being produced at least partially on the part of the second electrode which extends over the insulating block.

23. A process for the production of a capacitive hygrometer, of the type in which onto a layer of a conductive material forming the first electrode is deposited a layer of insulating material comprising a polymer whose dielectric constant varies with the quantity of water absorbed, then on said dielectric material layer is deposited a second conductive layer forming the second electrode which is made permeable to water, wherein it comprises the steps of disposing an insulating block upon said first electrode, depositing the dielectric material on substantially the entire extent of the first electrode and on the insulating block, depositing the second conductive layer on the dielectric layer so that at least one part of the second conductive layer extends over the insulating block, forming an oxide layer on the face of one said electrodes adjacent said dielectric layer and producing first and second electrical contacts with the first and second electrodes respectively, said second contact being produced at least partially on the part of the second electrode which extends over the insulating block.

24. A process according to claim 22, wherein the thickness of the insulating block is substantially the same as that of the layer forming the first electrode.

* * * * *

UNITED STATES PATENT AND TRADEMARK OFFICE
CERTIFICATE OF CORRECTION

PATENT NO. : 4,482,581
DATED : November 13, 1984
INVENTOR(S) : Andre Lorin et al.

It is certified that error appears in the above—identified patent and that said Letters Patent is hereby corrected as shown below:

On the title page;

The following should be added to the face of the patent under the heading "References Cited":

FOREIGN PATENT DOCUMENTS

| | | |
|---|---|---|
| 2938434 | 11/80 | Fed. Rep. of Germany |
| 2043908 | 3/79 | Great Britain |

Signed and Sealed this

Twenty-fifth Day of June 1985

[SEAL]

*Attest:*

DONALD J. QUIGG

*Attesting Officer*    Acting Commissioner of Patents and Trademarks